United States Patent [19]

Dygos

[11] 3,970,686
[45] July 20, 1976

[54] 5-(1,2,3,4-TETRAHYDRO-6-METHOXY-2-NAPHTHYL)-2-HYDROXY-1-METHYLCYCLOPENTANEETHANOLS AND ESTERS

[75] Inventor: John H. Dygos, Northbrook, Ill.

[73] Assignee: G. D. Searle & Co., Chicago, Ill.

[22] Filed: Mar. 31, 1975

[21] Appl. No.: 563,566

Related U.S. Application Data

[63] Continuation of Ser. No. 464,826, April 29, 1974, Pat. No. 3,907,905.

[52] U.S. Cl. .................... 260/476 C; 260/410.5; 260/488 CD; 260/515 R; 260/613 R; 424/308; 424/311; 424/312; 424/341

[51] Int. Cl.² .................. C07C 69/16; C07C 69/28; C07C 69/78

[58] Field of Search ....... 260/488 CD, 476 C, 410.5

[56] References Cited
UNITED STATES PATENTS
3,102,133  8/1963  Chinn ..................... 260/488 CD
FOREIGN PATENTS OR APPLICATIONS
1,243,243  8/1971  United Kingdom ......... 260/488 CD

*Primary Examiner*—Vivian Garner
*Attorney, Agent, or Firm*—John M. Brown

[57] ABSTRACT

Preparation and the antihypercholesterolemic activity of 5-(1,2,3,4-tetrahydro-6-methoxy-2-napthyl)-2-hydroxy-1-methylcyclopentaneethanols and esters thereof are disclosed.

7 Claims, No Drawings

5-(1,2,3,4-TETRAHYDRO-6-METHOXY-2-NAPHTHYL)-2-HYDROXY-1-METHYLCYCLOPENTANEETHANOLS AND ESTERS

The application for Letters Patent securing the invention herein described and claimed is a continuation of Applicant's copending application Ser. No. 464,826 filed Apr. 29, 1974 now U.S. Pat. No. 3,907,905.

This invention relates to 5-(1,2,3,4-tetrahydro-6-methoxy-2-naphthyl)-2-hydroxy-1-methylcyclopentaneethanols and esters thereof and to processes for their preparation. More particularly, this invention provides new, useful, and unobvious chemical compounds of the formula

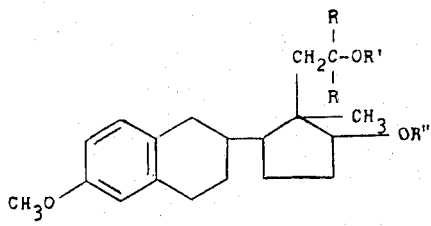

wherein R represents hydrogen or lower alkyl and R' and R'' each represent hydrogen or an esterifying moiety.

Typical of the lower alkyls represented by R are methyl, ethyl, propyl, isopropyl, butyl, isobutyl, sec.-butyl, tert.-butyl, pentyl, neopentyl, hexyl, isohexyl, heptyl, and like monovalent, saturated, acyclic, straight- or branched-chain, hydrocarbon groupings of the formula -$C_nH_{2n+1}$ wherein n represents a positive integer less than 8. Among these groupings, methyl is preferred.

Typical of the esterifying moieties represented by R' and R'' are lower alkanoyl, i.e.,

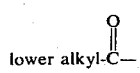

the lower alkyl constituent being defined as above, and benzoyl. Preferably, when R represents lower alkyl, R' represents hydrogen.

The compounds to which this invention relates are useful by reason of their valuable biological properties. In particular, they are antihypercholesterolemic, as is demonstrable by the standardized procedure set forth in U.S. Pat. No. 3,501,506.

Those skilled in the art will recognize from their formula that the compounds of this invention occur in a plurality of configurations such that the 2-oxy function is either cis or trans with respect to the ethanolic constituent. It does not appear, however, that configuration is critical to utility. For instance, both the cis (1S,2S,5S) and trans (1S,2R,5S) isomers of Examples 1B and 2B hereinafter respectively, are antihypercholesterolemic at 10 mg orally when used as described in U.S. Pat. No. 3,501,506.

Preparation of 5-(1,2,3,4-tetrahydro-6-methoxy-2-naphthyl)-2-hydroxy-1-methylcyclopentaneethanol proceeds by contacting 5-(1,2,3,4-tetrahydro-6-methoxy-2-naphthyl)-2-hydroxy-1-methylcyclopentaneacetic acid or a lower alkanoyl ester thereof with lithium tetrahydroaluminate(1-) in a solvent such as tetrahydrofuran (THF) or a mixture of THF and diethyl ether. Configuration of the product corresponds to that in the acid thus reduced. Where the hydroxy acid does not persist as such, but instead lactonizes, the lactone can be substituted for the hydroxy acid as starting material.

Preparation of a 5-(1,2,3,4-tetrahydro-6-methoxy-2-naphthyl)-2-hydroxy-α,α-di(lower alkyl)-1-methylcyclopentane-ethanol proceeds by contacting a lower alkyl ester or lactone of 5-(1,2,3,4-tetrahydro-6-methoxy-2-naphthyl)-2-hydroxy-1-methylcyclopentaneacetic acid with (lower alkyl)-magnesium bromide in THF or THF and ether, configuration of the product again being determined by the starting material used.

Esterification of the hydroxyl in 5-(1,2,3,4-tetrahydro-6-methoxy-2-naphthyl)-2-hydroxy-1-methylcyclopentaneacetic acid by conventional procedures such as contacting with acid chloride in pyridine, followed by reduction of the carboxyl to hydroxyl via contact with borane in THF affords a corresponding mono ester of this invention. The analogous α,α-di(lower alkyl) mono ester of the invention, on the other hand, is obtained by contacting a 5-(1,2,3,4-tetrahydro-6-methoxy-2-naphthyl)-2-hydroxy-α,α-di(lower alkyl)-1-methylcyclopentaneethanol with acid chloride in pyridine.

Contacting (1S, 2S, 5S) -5-(1,2,3,4-tetrahydro-6-methoxy-2-naphthyl)-2-hydroxy-1-methylcyclopentaneacetic acid with butyl vinyl ether in THF containing methanesulfonic acid affords the stereochemically corresponding α-butoxyethyl 2-(α-butoxyethoxy)-5-(1,2,3,4-tetrahydro-6-methoxy-2-naphthyl)-1-methylcyclopentaneacetate, in which the ester linkage is cleaved and the carboxyl reduced to hydroxy by contacting with lithium tetrahydroaluminate (1−) in THF. From the resultant alcohol, on esterification with acid chloride or anhydride in pyridine, followed by cleavage of the ether linkage via hydrochloric acid in acetone, the corresponding mono ester of the invention wherein the ester grouping is on the ethanolic side chain eventuates. Contacting such a mono ester with acid chloride or anhydride affords a di-ester of the invention.

The following examples described in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and specific rotations refer to the D line of sodium and were determined in solution at room temperatures.

EXAMPLE 1

A. To a solution of 4.54 g of (1S,2S,5S)-2-acetoxy-5-(1,2,3,4-tetrahydro-6-methoxy-1-oxo-2-naphthyl)-1-methyl-cyclopentaneacetic acid [J. Chem. Soc., 1968, 2603] in 250 ml of ethanol is added 0.5 g of 5% palladium-on-charcoal, and the resultant mixture is agitated in a hydrogen atmosphere at 50° for 72 hours. The mixture thus obtained is filtered. The filtrate is stripped of solvent by vacuum distillation, affording a yellow oil which crystallizes on standing. The crystalline material is taken up in benzene; and the benzene solution is chromatographed on silica gel, using benzene and mixtures thereof with increasing amounts of ethyl acetate as developing solvents. From an eluate comprising 10% ethyl acetate in benzene, on evaporation of solvent and recrystallization of the residue from a mixture of ethyl acetate and hexane, (1S,2S,5S)-2-acetoxy-5-(1,2,3,4-tetrahydro-6-methoxy-2-naphthyl)-1-methylcyclopentaneacetic acid melting at 125°–127° and further characterized by a specific rotation of + 50° is obtained.

B. To a slurry of 0.420 g of lithium tetrahydroaluminate(1-) in 400 ml of ether is slowly added, with stirring, a solution of 0.780 g of (1S,2S,5S)-2-acetoxy-5-(1,2,3,4-tetrahydro-6-methoxy-2-naphthyl)-1-methylcyclopentaneacetic acid in a mixture of 10 ml of diethyl ether and 5 ml of THF. When the addition is complete, stirring is continued at room temperature for 18 hours, whereupon 1.7 ml of aqueous 5% sodium hydroxide followed by 40 ml of dichloromethane is introduced. The resultant mixture is filtered. Solvent is stripped from the filtrate by vacuum distillation, leaving a white solid residue which, crystallized from a mixture of benzene and hexane, affords (1S,2S,5S)-5-(1,2,3,4-tetrahydro-6-methoxy-2-naphthyl)-2-hydroxy-1-methylcyclopentaneethanol melting at 151°–153° further characterized by a specific rotation of +62°.

EXAMPLE 2

A. To a slurry of 75 g of 20-mesh granular zinc metal in a mixture of 10 ml of concentrated hydrochloric acid with 200 ml of water is added, with stirring, 7.50 g of mercuric chloride. Stirring is continued for 10 minutes, whereupon the liquid is decanted; and the zinc amalgam thus formed is washed thoroughly with water. The amalgam is then added, with stirring, to a solution of (1S,2S,5S)-2-acetoxy-5-(1,2,3,4-tetrahydro-6-methoxy-1-oxo-2-naphthyl)-1-methylcyclopentaneacetic acid in 450 ml of hot acetic acid. Approximately 75 ml of concentrated hydrochloric acid is introduced; and the resultant mixture is refluxed for 20 minutes, whereupon a further 75 ml of hydrochloric acid is added at a rate such as to require 1 ½ hours during which refluxing is continued. The reaction mixture is then concentrated by evaporating in a stream of nitrogen, and the concentrate is poured into 2 liters of water. The resultant mixture is extracted with ethyl acetate. The extract is dried over magnesium sulfate, treated with decolorizing charcoal, and filtered. Solvent is removed from the filtrate by vacuum distillation. The residue is dissolved in benzene; and the benzene solution is chromatographed on silica gel, using benzene and mixtures thereof with increasing amounts of ethyl acetate as developing solvent. From an eluate comprising 2% ethyl acetate in benzene, on evaporation of solvent and recrystallization of the residue from a mixture of benzene and hexane, cis-hexahydro-4-(1,2,3,4-tetrahydro-6-methoxy-2-naphthyl)-3a-methyl-2H-cyclopenta[b]furan-2-one melting at 84°–86° is obtained.

B. To a suspension of 0.250 g of lithium tetrahydroaluminate(1-) in 20 ml of THF is slowly added, with stirring, a solution of 0.945 g of cis-hexahydro-4-(1,2,3,4-tetrahydro-6-methoxy-2-naphthyl)-3a-methyl-2H-cyclopenta-[b]furan-2one in 30 ml of THF. The resultant mixture is stirred at room temperatures for 3 hours, whereupon 1 ml of water is added dropwise and stirring at room temperatures then continued overnight. The mixture thus obtained is filtered, and the insoluble material thus separated is thoroughly washed with hot THF. Washings are combined with the original filtrate and solvents stripped therefrom by vacuum distillation. The residue, crystallized from a mixture of benzene and hexane, affords (1S,2R,5S)-5-(1,2,3,4-tetrahydro-6-methoxy-2-naphthyl)-2-hydroxy-1-methylcyclo-pentaneethanol melting in the range 105°–110°.

EXAMPLE 3

To a solution of 3.33 g of (1S,2S,5S)-2-acetoxy-5-(1,2,3,4-tetrahydro-6-methoxy-2-naphthyl)-1-methyl-cyclo-pentaneacetic acid in 50 ml of methanol is added a solution of 3.00 g of potassium hydroxide in 15 ml of water. The resultant solution is refluxed for 2 hours, then diluted with 250 ml of water. Clarification is effected by filtration. The filtrate is acidified with hydrochloric acid. A solid precipitates which, isolated by filtration and recrystallized from a mixture of ethyl acetate and hexane, affords (1S,2S,5S)-5-(1,2,3,4-tetrahydro-6-methoxy-2-naphthyl)-2-hydroxy-1-methylcyclopentaneacetic acid melting at approximately 141.5°–142.5°. The product has a specific rotation of +65°.

B. To a solution of 0.318 g of (1S,2S,5S)-5-(1,2,3,4-tetrahydro-6-methoxy-2-naphthyl)-2-hydroxy-1-methylcyclopentaneacetic acid in 15 ml of pyridine is added 0.227 g of propioyl chloride. The resultant mixture is stirred at room temperatures for 6 hours, then poured onto 25 volumes of ice. The resultant mixture is acidified with hydrochloric acid, whereupon the aqueous phase is extracted with ether. The ether extract is dried over magnesium sulfate and then stripped of solent by vacuum distillation. The residue is (1S,2S,5S)-5-(1,2,3,4-tetrahydro-6-methoxy-2-naphthyl)-1-methyl-2-propionyloxycyclopentaneacetic acid.

C. To a solution of 0.374 g of (1S,2S,5S)-5-(1,2,3,4-tetrahydro-6-methoxy-2-naphthyl)-1-methyl-2-propionyloxycyclopentaneacetic acid in 25 ml of THF is slowly added, with stirring, 1 ml of a 1.0 molar solution of borane in THF. The resultant mixture is stirred at room temperatures for 1 hour, whereupon 50 ml of water is slowly introduced and stirring at room temperature is continued thereafter for 2 hours. The mixture thus obtained is extracted with ether. The ether extract is dried over magnesium sulfate and stripped of solvent by vacuum distillation. The residue is (1S,2S, 5S)-5-(1,2,3,4-tetrahydro-6-methoxy-2-naphthyl)-1-methyl-2-propionyl-oxycyclopentaneethanol.

EXAMPLE 4

A. Substitution of 0.420 g of benzoyl chloride for the propionyl chloride called for in Example 3B affords, by the procedure there detailed, (1S,2S,5S)-2-benzoyloxy-5-(1,2,3,4-tetrahydro-6-methoxy-2-naphthyl)-1-methylcyclo-pentaneacetic acid.

B. Substitution of 0.372 g of (1S,2S,5S)-2-benzoyloxy-5-(1,2,3,4-tetrahydro-6-methoxy-2naphthyl)-1-methyl-cyclopentaneacetic acid for the (1S,2S,5S)-5-(1,2,3,4-tetrahydro-6-methoxy-2-naphthyl)-1-methyl-2-propionyloxy-cyclopentaneacetic acid called for in Example 3C affords, by the procedure there detailed, (1S,2S,5S)-2-benzoyloxy-5-(1,2,3,4-tetrahydro-6-methoxy-2-naphthyl)-1-methyl-cyclopentaneethanol.

EXAMPLE 5

A. To a solution of 2.57 g of (1S,2S,5S)-5-(1,2,3,4-tetrahydro-6-methoxy-2-naphthyl)-2-hydroxy-1-methylcyclopentaneacetic acid in 15 ml of THF is added 1.70 g of butyl vinyl ether and 3 drops of 10% (V/V) solution of methanesulfonic acid in THF. The resultant mixture is stirred at room temperatures for 4 ½ hours and then added dropwise, with continued stirring, to a suspension of 0.500 g of lithium tetrahydroaluminate (1-) in 20 ml of THF. The mixture thus obtained is stirred at room temperatures for 24 hours, whereupon 2.0 ml of aqueous 5% sodium hydroxide is added dropwise, followed by 50 ml of diethyl ether. Insoluble solids are filtered out and thoroughly washed with diethyl ether. Washings and the original filtrate are combined and stripped of solvent by vacuum distillation. The residue is (1S,2S,5S)-2-(α-butoxy-ethoxy)-5-(1,2,3,4-tetrahydro-6-methoxy-2-naphthyl)-1-methyl-cyclopentaneethanol.

B. A solution of 0.405 g of (1S,2S,5S)-2-(α-butoxyethoxy)-5-(1,2,3,4-tetrahydro-6-methoxy-2-naphthyl)-1-methyl-cyclopentaneethanol in 3 ml of acetic anhydride and 12 ml of pyridine is stirred at room temperatures for 16 hours, then poured into 100 ml of aqueous (0% sodium bicarbonate. The resultant mixture is extracted with ether. The ether extract is stripped of solvent by vacuum distillation, and to the residue is added a solution consisting of 20 ml of acetone, 5 ml of water, and 0.5 ml of concentrated hydrochloric acid. The mixture thus obtained is stirred for 1 hour at room temperatures, then poured into 100 ml of water. The resultant mixture is extracted with ether. The ether extract is dried over magnesium sulfate and stripped of solvent by vacuum distillation. The residue is (1S,2S,5S)-5-(1,2,3,4-tetrahydro-6-methoxy-2-naphthyl)-2-hydroxy-1-methylcyclo-pentaneethyl acetate.

EXAMPLE 6

To a solution of 0.405 g of (1S,2S,5S)-2-(α-butoxyethoxy)-5-(1,2,3,4-tetrahydro-6-methoxy-2-naphthyl)-1-methyl-cyclopentaneethanol in 50 ml of benzene and 1 ml of pyridine is added a solution of 0.280 g of benzoyl chloride in 10 ml of benzene. The resultant solution is stirred at room temperatures for 4 hours, then washed with aqueous 10% sodium bicarbonate and thereupon stripped of solvent by vacuum distillation. To the residue is added a solution consisting of 20 ml of acetone, 5 ml of water, and 0.5 ml of concentrated hydrochloric acid. This mixture is stirred at room temperatures for 1 hour, then partitioned between water and ether. The ether phase is separated, dried over magnesium sulfate, and stripped of solvent by vacuum distillation. The residue is (1S,2S,5S)-5-(1,2,3,4-tetrahydro-6-methoxy-2-naphthyl)-2-hydroxy-1-methyl-cyclopentaneethyl benzoate.

EXAMPLE 7

To a solution of 0.335 g of (1S,2S,5S)-5-(1,2,3,4-tetrahydro-6-methoxy-2-naphthyl)-2-hydroxy-1-methyl-cyclo-pentaneethyl acetate in 20 ml of benzene and 1 ml of pyridine is added a solution of 0.280 g of benzoyl chloride in 10 ml of benzene. The resultant mixture is stirred at room temperatures for 4 hours, then consecutively washed with 5% hydrochloric acid and aqueous 10% sodium bicarbonate, and finally dried over magnesium sulfate. Removal of solvent by vacuum distillation affords (1S,2S,5S)-2-benzoyloxy-5-(1,2,3,4-tetrahydro-6-methoxy-2-naphthyl)-1-methylcyclo-pentaneethyl acetate as the residue.

EXAMPLE 8

A. A solution of 2.19 g of (1S,2S,5S)-5-(1,2,3,4-tetrahydro-6-methoxy-2-naphthyl)-2-hydroxy-1-methyl-cyclo-pentaneacetic acid and 5 ml of 2,2-dimethoxypropane in 40 ml of methanol containing 0.05 g of p-toluenesulfonic acid monohydrate is refluxed for 18 hours. The resultant solution is partitioned between aqueous 5% sodium bicarbonate and ether. The ether phase is separated, dried over magnesium sulfate, and stripped of solvent by vacuum distillation. The residue is crystallized from a mixture of acetone and hexane to give methyl (1S,2S,5S)-5-(1,2,3,4-tetrahydro-6-methoxy-2-naphthyl)-2-hydroxy-1-methylcyclopentaneacetate melting at approximately 86°–87°.

B. To a solution of 0.600 g of methyl (1S,2S,5S)-5-(1,2,3,4-tetrahydro-6-methoxy-2-naphthyl)-2-hydroxy-1-methylcyclopentaneacetate in 50 ml of diethyl ether is added a solution of 0.596 g of methylmagnesium bromide in 5 ml of diethyl ether. The resultant mixture is stirred at room temperatures for 1 hour, then diluted with 5 volumes of water. The mixture thus obtained is partitioned between 5% hydrochloric acid and ether. The aqueous phase is extracted with benzene; and the benzene extract is combined with the ether, dried over magnesium sulfate, and stripped of solvent by vacuum distillation. The residue, crystallized from a mixture of benzene and hexane, affords (1S,2S,5S)-5-(1,2,3,4-tetrahydro-6-methoxy-2-naphthyl)-2-hydroxy-α,α,1-trimethylcyclopentaneethanol melting at 123°–125°.

EXAMPLE 9

Substitution of 0.332 g of (1S,2S,5S)-5-(1,2,3,4-tetrahydro-6-methoxy-2-naphthyl)-2-hydroxy-α,α,1-trimethylcyclopentaneethanol and 0.235 g of acetyl chloride for the (1S,2S,5S)-5-(1,2,3,4-tetrahydro-6-methoxy-2-naphthyl)-2-hydroxy-1-methylcyclopentaneacetic acid and propionyl chloride, respectively, called for in Example 3B affords, by the procedure there detailed, (1S,2S,5S)-2-acetoxy-5-(1,2,3,4-tetrahydro-6-methoxy-2-naphthyl)-α,α,1-trimethylcyclopentane-ethanol.

EXAMPLE 10

To a solution of 3.576 g of methylmagnesium bromide in 30 ml of ether is slowly added, with stirring, a solution of 2.00 g of cis-hexahydro-4-(1,2,3,4-tetrahydro-6-methoxy-2-naphthyl)-3a-methyl-2H-cyclopenta[b]furan-2-one in 40 –of THF. The reaction mixture is stirred at room temperatures for 2 ½ hours, whereupon 100 ml of water is cautiously introduced, followed by 10 ml of concentrated hydrochloric acid. The mixture thus obtained is extracted with ether. The ether extract is dried over magnesium sulfate and then stripped of solvent by vacuum distillation. The residue is a yellowish oil, which is taken up in benzene. The benzene solution is treated with decolorizing charcoal and then filtered. The filtrate is concentrated to approximately 10 ml by distillation at 78°–80°, whereupon the hot concentrate is diluted with approximately 30 ml of hexane. On chilling, (1S,2R,5S)-5-(1,2,3,4-tetrahydro-6-methoxy-2-naphthyl)-2-hydroxy-α,α,1-trimethylcyclopentaneethanol precipitates. The product thus obtained, isolated by filtration and dried in air, sinters at 111° and melts at 113°–115°.

What is claimed is:
1. A compound of the formula

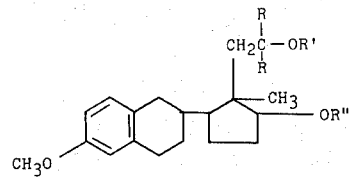

wherein R represents hydrogen or methyl; R' represents hydrogen when R represents methyl, otherwise R' represents hydrogen, lower alkanoyl, or benzoyl; R'' represents hydrogen, or lower alkanoyl, or benzoyl; and R' and R'' do not simultaneously represent hydrogen.

2. A compound according to claim 1 which is (1S,2S,5S)-5-(1,2,3,4-tetrahydro-6-methoxy-2-naphthyl)-1-methyl-2-propionyloxycyclopentaneethanol.

3. A compound according to claim 1 which is (1S,2S,5S)-2-benzoyloxy-5-(1,2,3,4-tetrahydro-6-methoxy-2-naphthyl)-1-methylcyclopentaneethanol.

4. A compound according to claim 1 which is (1S,2S,5S)-5-(1,2,3,4-tetrahydro-6-methoxy-2-naphthyl)-2-hydroxy-1-methylcyclopentaneethyl acetate.

5. A compound according to claim 1 which is (1S,2S,5S)-5-(1,2,3,4-tetrahydro-6-methoxy-2-naphthyl)-2-hydroxy-1-methylcyclopentaneethyl benzoate.

6. A compound according to claim 1 which is (1S,2S,5S)-2-benzoyloxy-5-(1,2,3,4-tetrahydro-6-methoxy-2-naphthyl)-1-methylcyclopentaneethyl acetate.

7. A compound according to claim 1 which is (1S,2S,5S)-2-acetoxy-5-(1,2,3,4-tetrahydro-6-methoxy-2-naphthyl)-α,α,1-trimethylcyclopentaneethanol.

* * * * *

UNITED STATES PATENT AND TRADEMARK OFFICE
CERTIFICATE OF CORRECTION

PATENT NO. : 3,970,686
DATED : July 20, 1976
INVENTOR(S) : John H. Dygos

It is certified that error appears in the above-identified patent and that said Letters Patent are hereby corrected as shown below:

Front Page, Element [54], "METHYLCYCLOPENTANEETHANOLS AND" should read -- METHYLCYCLOPENTANEETHANOL --.

Column 1, lines 3 and 4, "METHYLCYCLOPENTANEETHANOLS AND" should read -- METHYLCYCLOPENTANEETHANOL --.

Column 2, line 39, "described" should read -- describe --.

Column 3, line 58, "2one" should read -- 2-one --.

Column 4, line 53, "2naphthyl" should read -- 2-naphthyl --.

Column 5, line 17, "(0%" should read -- 10% --.

Column 6, line 43, "40 -of" should read -- 40 ml of --.

Signed and Sealed this

Fifteenth Day of February 1977

[SEAL]

Attest:

RUTH C. MASON
Attesting Officer

C. MARSHALL DANN
Commissioner of Patents and Trademarks